United States Patent [19]

Glassman

[11] 4,299,225
[45] Nov. 10, 1981

[54] SURGICAL EXTRACTER

[75] Inventor: Jacob A. Glassman, Miami Beach, Fla.

[73] Assignee: The Southeastern Research Foundation, Miami Beach, Fla.

[21] Appl. No.: 33,478

[22] Filed: Apr. 26, 1979

[51] Int. Cl.³ .............................................. A61B 17/00
[52] U.S. Cl. .................................................. 128/328
[58] Field of Search ................ 128/328, 345, 356, 321

[56] References Cited
U.S. PATENT DOCUMENTS

| 3,108,593 | 10/1963 | Glassman | 128/328 |
| 3,108,594 | 10/1963 | Glassman | 128/328 |
| 3,137,298 | 6/1964 | Glassman | 128/328 |
| 4,046,150 | 9/1977 | Schwartz et al. | 128/328 |

Primary Examiner—Robert W. Michell
Assistant Examiner—Michael H. Thaler
Attorney, Agent, or Firm—Elmer L. Zwickel

[57] ABSTRACT

The invention relates to improvements in surgical instruments and is particularly concerned with the novel construction of an instrument for use in the dislodging and extraction of gall stones from the common bile duct irrespective of their size or degree of impactness.

5 Claims, 4 Drawing Figures

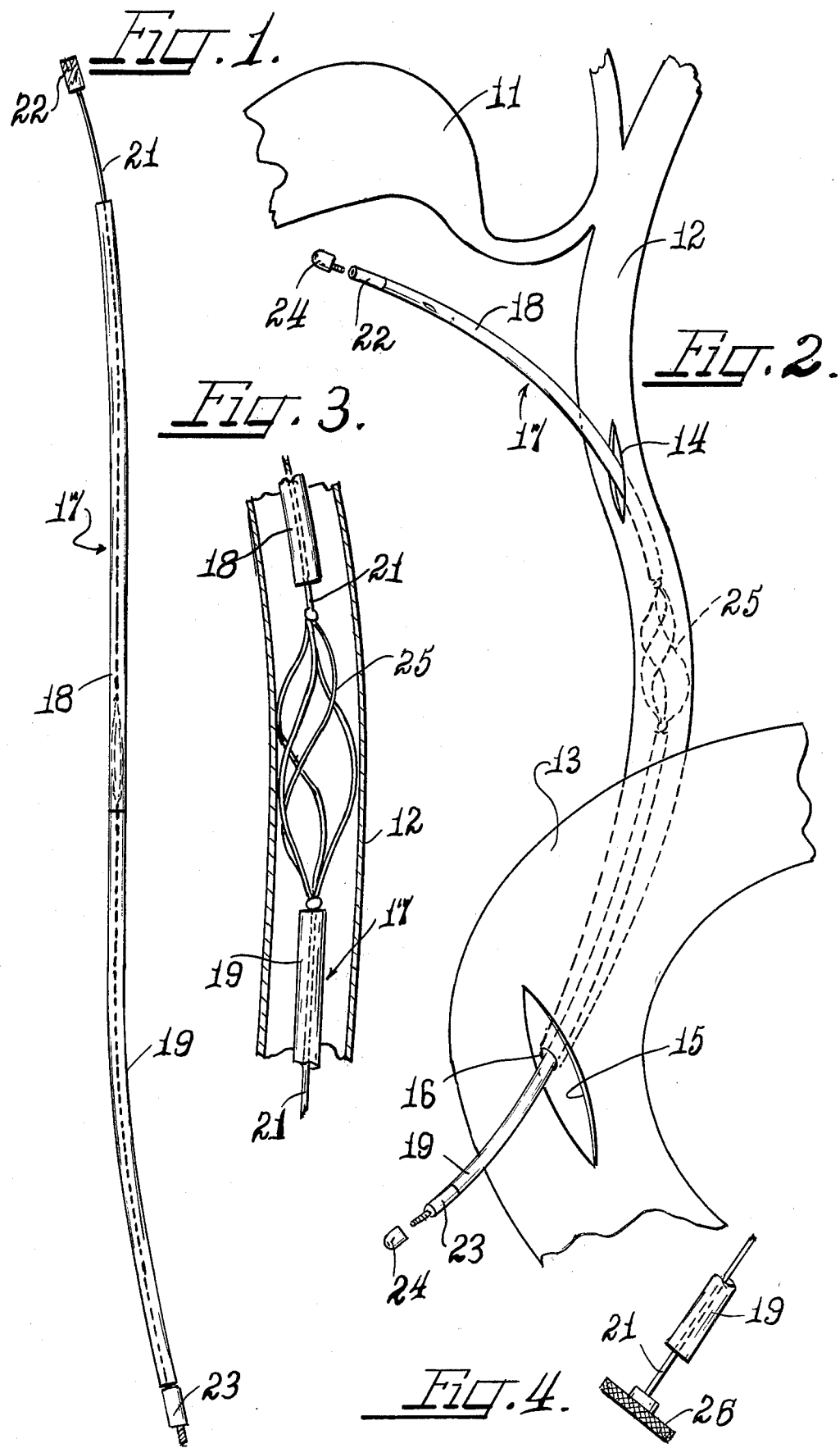

SURGICAL EXTRACTER

The novel instrument disclosed herein is of a character that is adapted to be drawn through, rotated, and/or reciprocated to and fro longitudinally in the common bile duct so as to engage with, dislodge and/or entrap a gall stone or stones for withdrawan from the duct. The employment of this type of instrument involves the practice of making a high level incised opening in the common bile duct and another incised opening in the duodenum in an area opposite to the termination of said duct in the duodenum for the entrance and exit of the instrument.

The stone dislodging and extracting instrument herein disclosed is a decided improvement in the instrument shown and claimed in U.S. Pat. No. 2,943,626, and is related to those shown and claimed in my U.S. No. Pat. 3,108,595, issued Oct. 29, 1963. In U.S. Pat. No. 2,943,626, the instrument, commercially known as the "Dormia Stone Dislodger", is characterized by having a catheter traversed by a metal rod which carries on one end, a flexible stainless steel wire basket or cage in the form of an helical bobbin spindle normally collapsed within the catheter and which is opened when the basket is pushed out through the other end of the catheter. This instrument is operable from one end only and only a common bile duct incision is required.

My prior U.S. Pat. No. 3,108,593, teaches an instrument that projects out through the bile duct opening and out through the doudenum opening so as to be manipulated from either of both ends, and it is used by sweeping the instrument through the bile duct or by recoprocating or rotating it. The cage or basket is expanded normally at all times and may be collapsed only by exerting a pull at either end of the instrument or at both ends simultaneously.

In the present disclosure, the advantageous features of both of the above instruments are combined with other features to make a more practical, efficient and safe instrument. More specifically, the improved instrument includes a wire probe having, substantially midway between its ends, a flexible stainless steel wire basket that is collapsed and concealed within two catheter-type sleeves at the time of inserting it into an incised opening. After insertion, one of the sleeves is withdrawn relative to the basket so as to expose same and permit it to expand into an open helical condition within the bile duct. It is not essential to put the instrument under tension; all that is required is manipulation of the helical wire basket.

In use of the instrument, the flexible shape-retaining probe, having a male coupling fitting on one end and a female coupling fitting at its other end, is inserted through the high level incised opening (choledochotomy) and fed into the common bile duct, and as it emerges through the sphincter of Oddi it is projected out through the incised opening in the cuodenum (duodenostomy).

After the instrument is in place within the common bile duct, with both ends projecting outwardly through the respective incised openings, the exposed end of the upper plastic catheter-type sleeve is then manually engaged and withdrawn until its outer end abuts the female fitting, whereupon the basket is released and can then expand into a fully open position comparable with the diameter of the common duct. The instrument may be then moved by short to and fro motion within the bile duct and, if advisable, it may be rotated all so as to disengage a stone or stones from the wall of the duct and entrap it snugly within the basket. When the instrument is withdrawn from the duct through either the high level or low level incised openings, the entrapped stone or stones are withdrawn, firmly enclosed within the adjusted basket.

The presence of the male and female fittings on the ends of the probe is primarily for the purpose of limiting outward movement of the catheter type enclosures and for manual engagement while manipulating the instrument. They also serve to afford means for attaching handles or supplemental stone loosening implements, such as special brushes and balloon as are shown in my aforesaid U.S. Pat. No. 3,108,594.

In view of the foregoing preliminary disclosure, various objects of the invention are to provide a novel instrument of the character referred to; to afford novel reliable readily insertable and manipulatable means to remove difficultly positioned gall stones from the common bile duct efficiently; to provide a stone extractor with means to normally protect and conceal it's stone extracting and entrapping basket prior to its use to provide a gall stone remover which can be manipulated manually from either or both ends while within the lumen of the common bile duct.

With the foregoing and such other objects and advantages of the invention as may become apparent as the description proceeds, the invention pertains to the novel method of stone removal and to an instrument embodying novel features of construction, arrangement of parts hereinafter fully described, illustrated in the accompanying drawings, and particularly pointed out in the appended claims.

In the Drawings:

FIG. 1 is an elevational view of the extracter instrument showing the basket collapsed and enclosed within the catheter-type sleeves.

FIG. 2 is a schematic representation of the common bile duct and associated organs, illustrating placement of the flexible instrument within the bile duct and with the basket expanded.

FIG. 3 is an enlarged longitudinal sectional view of the medial portion of the instrument and bile duct, showing one of the plastic catheter-like sleeves withdrawn from over the basket.

FIG. 4 is a fragmentary view of one end of the instrument having a knurled disk on one end to facilitate rotation of the basket.

Referring generally to the exemplary disclosures in the accompanying drawings, the improved instrument is so designed that it may be inserted through an incised opening in the duodenum at the level of the sphincter of Oddi, or through the upper incised opening in the common bile duct (choledochotomy).

The ideal manipulation of the instrument is accomplished by initial insertion through the high level incised opening of the shape-retaining probe enclosed within a plastic catheter-like sleeve. The probe preferably is fabricated from a thin relatively firm but pliable wire-like length of silver, copper, or other pliable metal or plastic bar stock. The probe, which has a central portion defining a helical cage or basket, has it's ends extending out from the respective ends of the plastic catheter-like sleeves. One end of the probe carries a male fitting and the other end carries a female fitting that can be used to attach other auxiliary instruments useful in gall stone removal. The plastic catheter-like sleeve is comprised of two parts, being circumferentially split in the region of the basket and it is of an overall length substantially shorter than the distance between the two end fittings on the probe. The stone dislodging and removing instrument is characterized by its ability to be drawn to and fro within the common bile duct so as to extend or restrict the dislodged and entrapping basket.

Referring now particularly to the exemplary disclosure illustrated in the drawing, there is shown, rather diagrammatically, the anatomy of a gall bladder 11 and common bile duct 12 which opens into the duodenum 13. In the herein disclosed means for stone removal, an incised opening 14 is made at a high level in the common bile duct (choledochostomy) and a second incised opening 15 is made in the duodenum (duodenotomy) opposite to the site of the sphincter of Oddi 16.

The instrument 17 shown in the drawings is comprised of two plastic catheter-like sleeves 18 and 19 of different lengths which are telescoped for free sliding over opposite ends of a wire-like body 21 of thin relatively firm but pliable material such as silver, copper, steel, or even plastic material. One end of the wire-like body 21 has a female fitting 22 and the other end carries a male fitting 23. These fittings afford means to attach auxiliary instruments, handles, or snub-nosed caps 24 or balloon catheters, such as are disclosed in my U.S. Pat. Nos. 3,108,594, and 3,108,593.

Midway the length of the wire-like body 21 there is provided three, four or more stainless steel strands of springy material which are twisted so as to form a helical basket 25. The strands are normally bowed out in their length portion radially from their axis. Thus, the basket tends to remain expanded as illustrated in FIG. 3, but because of it's flexibility and memory, it may be deformed into a substantially flat mass within the lumen of the catheter. Such deformation is required when the instrument is to be inserted into or withdrawn from the common bile duct by the lead flexible probe 21. To accomplish such collapse, the two catheter-like halves or sleeves 18-19 are of a total length less than the length of the basket and normally the sleeve 19 extends from the male fitting 23 to the related end of the basket 24. As shown in FIG. 1, the other sleeve 18 normally overlies and encloses the collapsed basket 25 and terminates short of the female fitting 22 by a length substantially equal to the length of the basket 25. Thus, after the instrument is in place in the common bile duct, the upper catheter-like sleeve 18 may be manually drawn toward the related end of the wire-like body, 21, thus exposing the basket 25 within the bile duct and allowing it to expand as in FIG. 2.

The instrument can now be moved to and fro by exerting a pull alternately on either end of the wire-like body 21, or the basket 25 may be rotated within the duct to engage, dislodge and/or entrap the stone. Further, by applying push or pull simultaneously on both ends of the instrument, the configuration of the basket 25 can be varied to better engage the stone. After the stone is engaged in the basket, the instrument can be withdrawn from the upper or lower incised opening 14-15, carrying the stone or stones with it.

In lieu of the fitting 23 on one end of the wire-like body 21, there may be provided, as shown in FIG. 4, an enlarged knurled disc 26, which is permanently secured to the wire-like body, thus affording readily engageable means for engaging and rotating the wire-like body and basket 25.

Although I have described a preferred embodiment of the invention, in considerable detail, it will be understood that the description thereof is intended to be illustrative rather than restrictive, as details of the structure may be modified or changed without departing from the spirit or scope of the invention. Accordingly, I do not desire to be restricted to the exact construction described.

I claim:

1. A common bile duct stone dislodging and extracting instrument comprising in combination:
   (a) a flexible probe including first and second flexible retaining wires
   (b) a springy strand bundle having said strands of substantially the same length and running in the same general direction and said strands each having right and left ends and a center portion
   (c) said bundle having a relaxed expanded position and a compressed collapsed position
   (d) said strands at their left ends coming together and secured to said first flexible retaining wire
   (e) said strands at their right ends coming together and secured to said second flexible retaining wire
   (f) said bundle when in said relaxed expanded position having its strands at their central portion normally spaced substantially from each other to form a stone receiving basket
   (g) said bundle when in said compressed collapsed position having its strands at their central portion in substantially abutting relation to each other to prevent escape of a retrieved stone
   (h) a first freely slideable and rotatable catheter sleeve telescoped over said first retaining wire and of a diameter sufficient to receive said bundle when in said compressed collapsed position and having its diameter substantially less than said bundle when in said relaxed expanded position
   (i) a second freely slideable and rotatable catheter sleeve telescoped over said second retaining wire and of a diameter sufficient to receive said bundle when in said compressed collapsed position and having its diameter substantially less than said bundle when in said relaxed expanded position
   (j) said first and second sleeves being independently movable with respect to each other toward and away from each other from a position of abutting contact to a distance at least equal to the length of said bundle
   (k) said first retaining wires including remote means for positioning said first catheter sleeve adjacent said left ends of said bundle strands
   (l) said second retaining wire including remote means for positioning said second catheter sleeve adjacent said right ends of said bundle strands
   (m) whereby said bundle, when in use, may be selectively covered and uncovered at any selected area along the length of said bundle.

2. A common bile duct stone dislodging and extracting instrument as in claim 1 and including:
   (a) stop means for each of said catheter sleeves on said flexible retaining wires to prevent separating said sleeves from said wires.

3. A common bile duct stone dislodging and extracting instrument as in claim 2 and wherein:
   (a) said stop means includes instrument coupling fittings.

4. A common bile duct stone dislodging and extracting instrument as in claim 3 and wherein:
   (a) said stop means includes a knurled handle.

5. A common bile duct stone dislodging and extracting instrument as in claim 1 and wherein:
   (a) said catheter sleeves each have a length substantially less than the distance between its respective one end of said bundle and its related stop means.

* * * * *